United States Patent
Nam et al.

(10) Patent No.: US 11,331,044 B2
(45) Date of Patent: May 17, 2022

(54) APPARATUS AND METHOD FOR MEASURING BIO-INFORMATION

(71) Applicant: SAMSUNG ELECTRONICS CO., LTD., Suwon-si (KR)

(72) Inventors: Jung Yong Nam, Hwaseong-si (KR); Joon Hyung Lee, Seongnam-si (KR); Ki Young Chang, Yongin-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 746 days.

(21) Appl. No.: 16/034,525

(22) Filed: Jul. 13, 2018

(65) Prior Publication Data

US 2019/0167199 A1 Jun. 6, 2019

(30) Foreign Application Priority Data

Dec. 1, 2017 (KR) ........................ 10-2017-0164565

(51) Int. Cl.
*A61B 5/1455* (2006.01)
*A61B 5/00* (2006.01)
*A61B 5/01* (2006.01)
*A61B 5/145* (2006.01)

(52) U.S. Cl.
CPC .............. *A61B 5/7203* (2013.01); *A61B 5/01* (2013.01); *A61B 5/1455* (2013.01); *A61B 5/14532* (2013.01); *A61B 5/14546* (2013.01); *A61B 5/489* (2013.01); *A61B 5/742* (2013.01); *A61B 5/7405* (2013.01); *A61B 5/7455* (2013.01); *A61B 5/14552* (2013.01); *A61B 2562/0238* (2013.01); *A61B 2562/043* (2013.01)

(58) Field of Classification Search
None
See application file for complete search history.

(56) References Cited

U.S. PATENT DOCUMENTS

| 297,736 A | 4/1884 | Wood |
| 815,687 A | 3/1906 | Davis |
| 6,061,583 A | 5/2000 | Ishihara et al. |

(Continued)

FOREIGN PATENT DOCUMENTS

| JP | 2012-66065 A | 4/2012 |
| KR | 10-2013-0028534 A | 3/2013 |

(Continued)

OTHER PUBLICATIONS

Communication dated Apr. 11, 2019, issued by the European Patent Office in counterpart European Application No. 18208230.5.

*Primary Examiner* — Marjan Fardanesh
(74) *Attorney, Agent, or Firm* — Sughrue Mion, PLLC

(57) ABSTRACT

An apparatus for non-invasively measuring bio-information is provided. The apparatus includes a plurality of light sources configured to emit light to a first region and a second region of an object, a detector configured to detect a first scattered light signal from the first region and a second scattered light signal from the second region and output a first electrical signal corresponding to the first scattered light signal and a second electrical signal corresponding to the second scattered light signal, and a processor configured to correct the first electrical signal based on the second electrical signal and measure bio-information based on a correction result.

27 Claims, 19 Drawing Sheets

(56) References Cited

U.S. PATENT DOCUMENTS

| | | |
|---|---|---|
| 6,569,104 B2 | 5/2003 | Ono et al. |
| 6,990,364 B2 | 1/2006 | Ruchti et al. |
| 7,215,982 B2 | 5/2007 | Oshima et al. |
| 7,756,569 B2 | 7/2010 | Hammer et al. |
| 8,535,221 B2 | 9/2013 | Saito |
| 9,498,158 B2 * | 11/2016 | Isaacson ............ A61B 5/14553 |
| 2006/0129038 A1 | 6/2006 | Zelenchuk et al. |
| 2008/0081968 A1 | 4/2008 | Numada et al. |
| 2012/0053434 A1 | 3/2012 | Saito |
| 2016/0015301 A1 | 1/2016 | Elliott et al. |
| 2016/0262626 A1 | 9/2016 | Pelosi et al. |
| 2017/0000350 A1 | 1/2017 | Kwon et al. |
| 2017/0215779 A1 | 8/2017 | Koide et al. |

FOREIGN PATENT DOCUMENTS

| | | |
|---|---|---|
| KR | 10-2017-0004607 A | 1/2017 |
| KR | 10-2017-0026840 A | 3/2017 |
| WO | 2016041073 A1 | 3/2016 |

\* cited by examiner

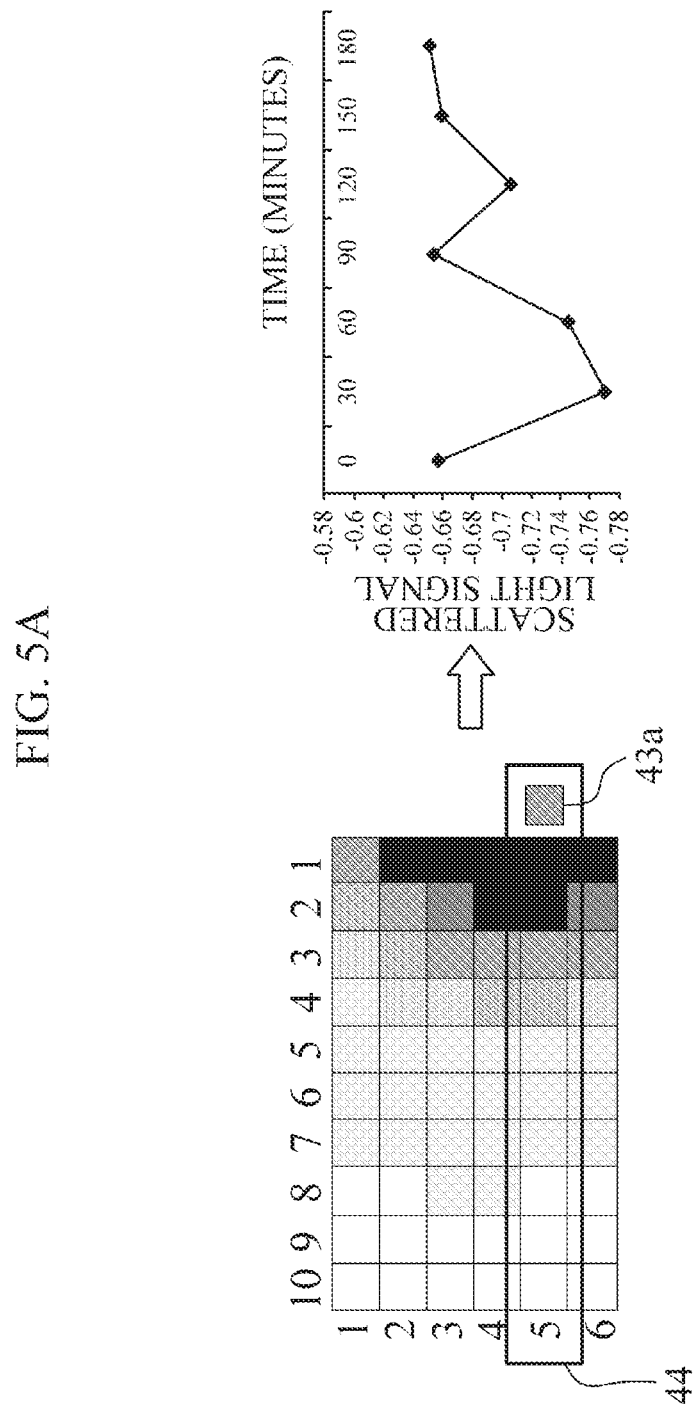

APPARATUS AND METHOD FOR MEASURING BIO-INFORMATION

CROSS-REFERENCE TO RELATED APPLICATION

This application claims priority from Korean Patent Application No. 10-2017-0164565, filed on Dec. 1, 2017, in the Korean Intellectual Property Office, the entire disclosure of which is incorporated herein by reference for all purposes.

BACKGROUND

1. Field

Exemplary embodiments of the present disclosure relate to an apparatus and method for non-invasively measuring bio-information, and more particularly, to a technology for measuring bio-information by correcting noise in information on a blood vessel region based on information on a non-blood vessel region.

2. Description of Related Art

Generally, a method of non-invasively measuring a triglyceride level is to estimate a concentration of triglyceride in blood by placing a measurement device composed of a light source and an optical sensor on a blood vessel and measuring scattered light signals having passed through the blood. Since a change of concentration of triglyceride in blood can be shown by a change of scattering coefficient of the blood, the change of scattering coefficient is acquired from the change of the scattered light signal and the concentration of triglyceride in blood is estimated based on the change of scattered coefficient. In order to more accurately estimate the concentration of triglyceride in blood through the change of the scattered light signal, only the scattering coefficient of the blood should cause the change of the scattered light signal, but, in reality, in addition to the change of the scattering coefficient of blood, various noise factors, such as physical/chemical changes of the skin, hemodynamics changes, and the like, may affect the scattered light signals.

SUMMARY

One or more exemplary embodiments provide an apparatus and method for non-invasively measuring bio-information.

According to an aspect of an exemplary embodiment, there is provided an apparatus to measure bio-information, the apparatus including a plurality of light sources configured to emit light to a first region and a second region of an object, a detector configured to detect a first scattered light signal reflected from the first region and a second scattered light signal reflected from the second region, and output a first electrical signal corresponding to the first scattered light signal and a second electrical signal corresponding to the second scattered light signal, and a processor configured to correct the first electrical signal based on the second electrical signal and measure the bio-information based on the corrected first electrical signal.

The first region may include a blood vessel region and the second region may include a non-blood vessel region.

The processor may be further configured to sequentially drive each of the plurality of light sources in a time-division manner.

The processor may be further configured to select a first light source among the plurality of light sources to emit light to the first region and a second light source from among the plurality of light sources to emit light to the second region from the plurality of light sources based on a preset criteria, and sequentially drive the first light source and the second light source to emit light.

The plurality of light sources may include at least one of a light emitting diode (LED) and a laser diode which emit light of an infrared band.

The detector may include a plurality of photodiode arrays disposed at different distances, respectively, from the plurality of light sources.

The processor may be further configured to correct the first electrical signal based on a rate of change of the second electrical signal at a time point.

The processor may be further configured to calculate a first scattering coefficient and a second scattering coefficient based on the first electrical signal and the second electrical signal, respectively, and correct the first scattering coefficient at a second time point based on a rate of change of the first scattering coefficient and a rate of change of the second scattering coefficient during a period from a first time point to the second time point.

The apparatus may further include a communication interface configured to transmit at least one of the first electrical signal, the second electrical signal, the corrected first electrical signal, and the measured bio-information to an external device.

The processor may be further configured to generate guide information corresponding to contact positions on the object of the plurality of light sources based on receiving a request to measure bio-information.

The guide information may include a guide image generated by superimposing visual information representing at least one of the first region and the second region or visual information representing at least one of the plurality of light sources on an image of the object.

The apparatus may further include an outputter configured to output at least one of the first electrical signal, the second electrical signal, the corrected first electrical signal, the measured bio-information, and the guide information.

The apparatus may further include a storage configured to store at least one of a value of the first electrical signal, a value of the second electrical signal, the corrected electrical signal, and the measured bio-information.

The bio-information may include at least one of blood glucose, cholesterol, triglyceride, skin temperature, protein, and uric acid.

According to an aspect of an exemplary embodiment, there is provided a method of measuring bio-information, the method including emitting light to a first region and a second region of an object by a plurality of light sources, detecting a first scattered light signal reflected from the first region and a second scattered light signal reflected from the second region, and outputting a first electrical signal corresponding to the first scattered light signal and a second electrical signal corresponding to the second scattered light signal, correcting the first electrical signal based on the second electrical signal, and measuring bio-information based on the corrected first electrical signal.

The first region may include a blood vessel region and the second region may include a non-blood vessel region.

The emitting of the light may include sequentially driving the plurality of light sources in a time-division manner.

The correcting of the first electrical signal may include correcting the first electrical signal based on a rate of change of the second electrical signal at a time point.

The correcting of the first electrical signal may include calculating a first scattering coefficient and a second scattering coefficient based on the first electrical signal and the second electrical signal, respectively, and correcting the first scattering coefficient at a second time point based on a rate of change of the first scattering coefficient and a rate of change of the second scattering coefficient during a period from a first time point to the second time point.

The method may further include outputting the measured bio-information.

The method may further include generating guide information corresponding to contact positions on the object of the plurality of light sources based on receiving a request to measure bio-information, and outputting the generated guide information.

According to an aspect of an exemplary embodiment, there is provided a wearable device including a main body, a strap connected to the main body and configured to fix the main body to an object, an optical apparatus disposed in the main body and configured to emit light to a first region and a second region of the object, detect a first scattered light signal reflected from the first region and a second scattered light signal reflected from the second region, and output a first electrical signal corresponding to the first scattered light signal and a second electrical signal corresponding to the second scattered light signal, and a processor disposed in the main body and configured to correct the first electrical signal based on the second electrical signal, and measure bio-information based on the corrected first electrical signal.

The first region may include a blood vessel region and the second region may include a non-blood vessel region.

The optical apparatus may include a plurality of light sources driven in a time-division manner by the processor, and a plurality of detectors disposed at different distances from the plurality of light sources, respectively.

The wearable device may further include a display disposed in the main body and configured to display guide information corresponding to a contact position on the object of the optical apparatus based on receiving a request to measure bio-information.

The wearable device may further include an image capturer disposed in the main body and configured to acquire an image of the object to generate the guide information.

The wearable device may further include a communication interface disposed in the main body and configured to receive an image of the object, to generate the guide information, from an external device.

The processor may be further configured to correct the first electrical signal based on a rate of change of the second electrical signal at a time point.

According to an aspect of an exemplary embodiment, there is provided an apparatus to measure bio-information, the apparatus including a first light source and a second light source configured to emit light to a first region and a second region of an object, respectively, a detector configured to detect a first scattered light signal reflected from the first region and a second scattered light signal reflected from the second region, and output a first electrical signal corresponding to the first scattered light signal and a second electrical signal corresponding to the second scattered light signal, and a processor configured to correct the first electrical signal based on the second electrical signal, and measure the bio-information based on the corrected first electrical signal, wherein the first region includes a blood vessel region and the second region includes a non-blood vessel region.

The first light source may include at least one light source and the second light source may include at least one light source.

The processor may be further configured to sequentially drive the first light source and the second light source in a time-division manner.

The processor may be further configured to correct the first electrical signal based on a rate of change of the second electrical signal at a time point.

The processor may be further configured to generate guide information corresponding to contact positions on the object of the first light source and the second light source based on receiving a request to measure bio-information.

The apparatus may further include an outputter configured to output at least one of the first electrical signal, the second electrical signal, the corrected first electrical signal, the measured bio-information, and the guide information, wherein the outputter includes at least one of a display, an audio, a haptic apparatus.

BRIEF DESCRIPTION OF THE DRAWINGS

These and/or other aspects will become apparent and more readily appreciated from the following description of the example embodiments, taken in conjunction with the accompanying drawings in which:

FIGS. 5A, 5B, 5C, 5D, 5E, and 5F are diagrams illustrating examples of measuring bio-information according to exemplary embodiments;

Figure 1:
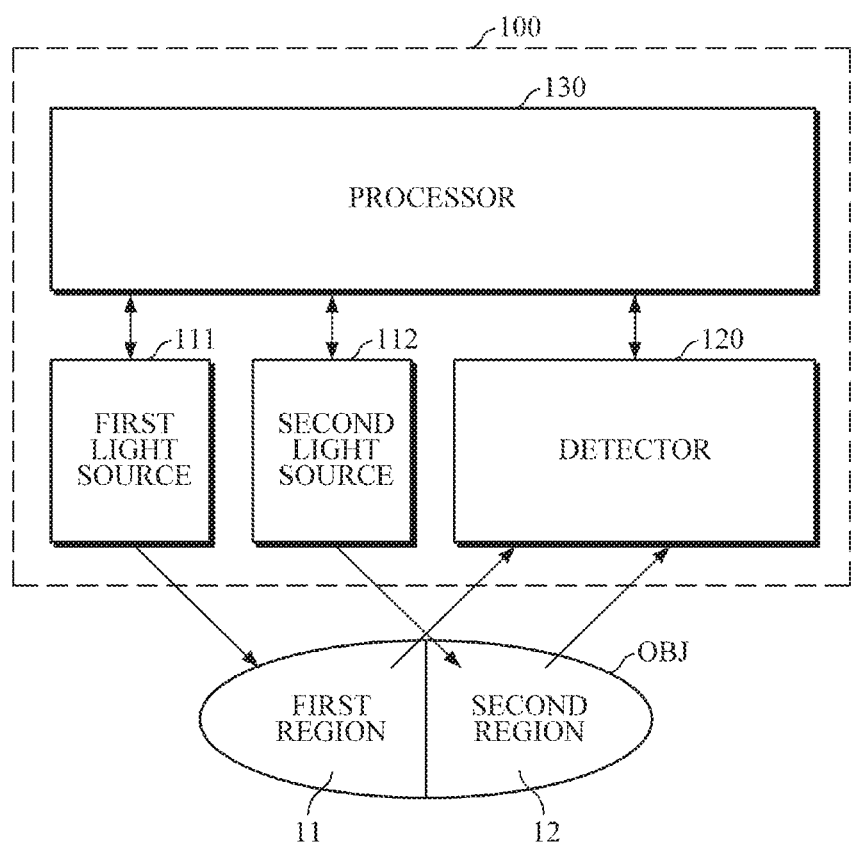
FIG. 1 is a block diagram illustrating an apparatus for measuring bio-information according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Reference will now be made in detail to example embodiments, of which are illustrated in the accompanying drawings. Aspects of the present disclosure may be embodied in many different forms and should not be construed as being limited to the exemplary embodiments set forth herein. Rather, these exemplary embodiments are provided so that the present disclosure will be thorough and complete and will fully convey the concept of the invention to those skilled in the art, and the present invention will only be defined by the appended claims. Like reference numerals refer to like elements throughout the specification.

It will be understood that, although the terms first, second, etc. may be used herein to describe various elements, these elements should not be limited by these terms. These terms are only used to distinguish one element from another. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, exemplary embodiments of an apparatus and method for measuring bio-information will be described in detail with reference to accompanying drawings.

Figure 2:
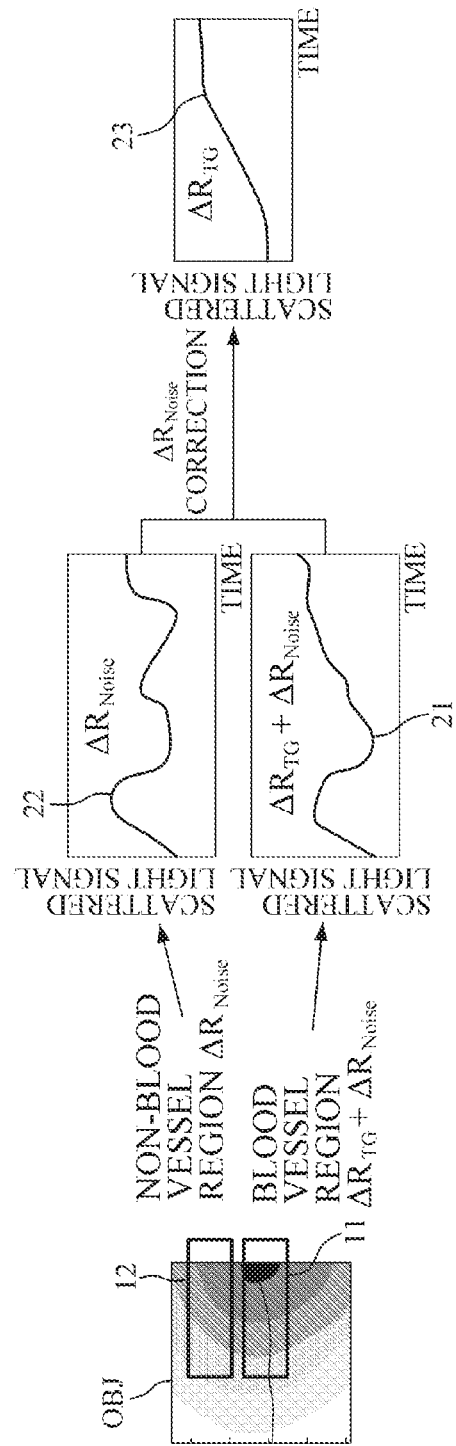
FIG. 2 is a diagram illustrating measuring bio-information according to an exemplary embodiment.

FIG. 1 is a block diagram illustrating an apparatus for measuring bio-information according to an exemplary embodiment. FIG. 2 is a diagram for describing measuring bio-information according to an exemplary embodiment.

Referring to FIG. 1, the apparatus 100 for measuring bio-information includes a first light source 111, a second light source 112, a detector 120, and a processor 130.

The first light source 111 and the second light source 112 emit light to an object OBJ under the control of the processor 130. In FIG. 1, two light sources 111 and 112 are shown, but the number of light sources is not particularly limited thereto. The first light source 111 and the second light source 112 may include, for example, a light emitting diode (LED), a laser diode (LD), or a phosphor. The first light source 111 and the second light source 112 may emit light sequentially in a time-division manner under the control of the processor 130. In this case, the first light source 111 and the second light source 112 may each emit light of a different wavelength, respectively. According to an exemplary embodiment, the plurality of light sources 111 and 112 may emit light of the same wavelength.

The first light source 111 and the second light source 112 may emit light to different regions 11 and 12 of the object OBJ. For example, a first light source 111 may emit light to a first region 11 of the object OBJ and a second light source 112 may emit light to a second region 12 of the object OBJ. The first light source 111 and the second light source 112 may emit light respectively to the first region 11 and the second region 12, sequentially with a predetermined time difference, under the control of the processor 130. In this case, the first region 11 of the object OBJ may be a blood vessel region through which a blood vessel passes, and the second region 12 may be a non-blood vessel region through which a blood vessel does not pass.

When three or more light sources are provided, the processor 130 may divide the light sources into a first group and a second group. At least some of the light sources belonging to the first group may emit light to the first region 11 and at least some of the light sources belonging to the second group may emit light to the second region 12.

The detector 120 detects a scattered light signal occurring when light is absorbed, scattered, or reflected by the object OBJ irradiated by the first light source 111 and the second light source 112. For example, the detector 120 may detect a first scattered light signal when light is scattered from the object OBJ after the first region 11 is irradiated by the first light source 111. In addition, when the detector 120 may detect a second scattered light signal when light is scattered from the object OBJ after the second region 12 is irradiated by the second light source 112.

The detector 120 may include a photodiode and may be formed by a plurality of photodiode arrays. The photodiodes may be disposed at different distances from the first light source 111 and the second light source 112. However, aspects of the present disclosure are not limited thereto, such that the detector 120 may include, for example, a photo transistor (PTr) and an image sensor, in addition to the photodiode.

When the first scattered light signal and the second scattered light signal are detected, the detector 120 may convert the first scattered light signal and the second scattered light signal into a first electrical signal and a second electrical signal, respectively. In this case, the first electrical signal and the second electrical signal may be electrical current signals. When the processor 120 receives a request for measuring bio-information, the processor 120 may control driving of the first light source 111 and the second light source 112. In this case, the processor 120 may sequentially drive the first light source 111 and the second light source 112 in a time-division manner according to a preset criterion. The processor 120 may receive the first electrical signal and the second electrical signal output from the detector 120, and measure the bio-information based on the received first and second electrical signals. In this case, the bio-information may include, for example, blood glucose, cholesterol, triglyceride, skin temperature, protein, uric acid, etc.

The apparatus 100 for measuring bio-information may further include an amplifier or an analog-to-digital converter. The first electrical signal and the second electrical signal output from the detector 120 may be amplified by the amplifier or converted into digital signals by the analog-to-digital converter and then input to the processor 130.

For example, referring to FIG. 2, a change of the first electrical signal 21 corresponding to the light emitted to the first region 11 of the object OBJ may include a change $R_{NOISE}$ by noise in addition to a change $R_{TG}$ by the triglyceride. On the other hand, a change of the second electrical signal 22 corresponding to the light emitted to the second region 12 may be a change by noise since the light has been emitted to the non-blood vessel region. The processor 120 may correct the first electrical signal 21 detected from the blood vessel region based on the second electrical signal 22 detected from the non-blood vessel region to remove noise and thereby acquire a third electrical signal 23 which reflects only the change due to the triglyceride in blood, and the processor 120 may measure the concentration of triglyceride in blood using the third electrical signal 23.

Figure 3:
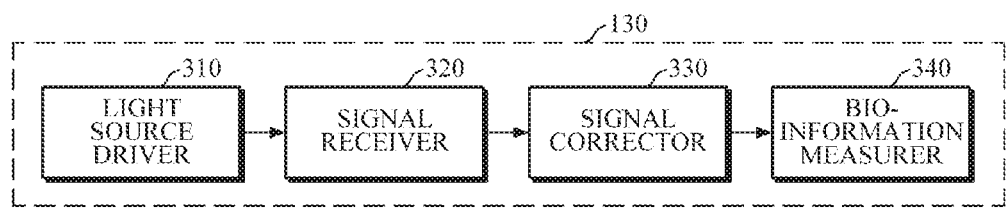
FIG. 3 is a block diagram illustrating a configuration of the processor according to the exemplary embodiment of FIG. 1.
Figure 4A:
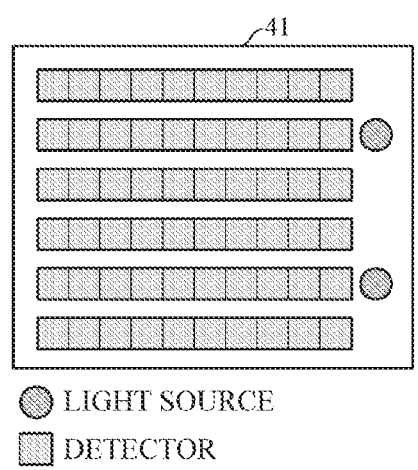
FIGS. 4A, 4B, and 4C are diagrams illustrating examples of configurations of the light source and the detector according to exemplary embodiments.
Figure 4B:
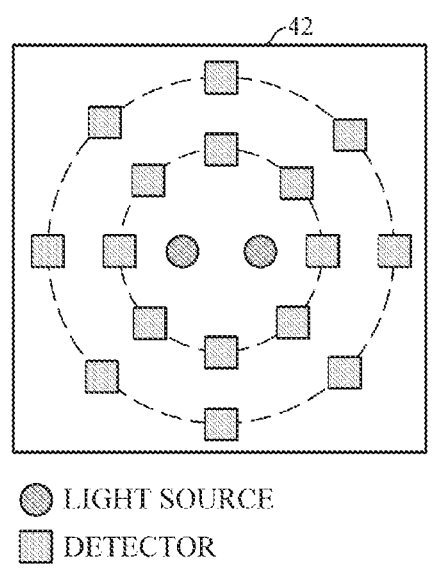
Figure 4C:
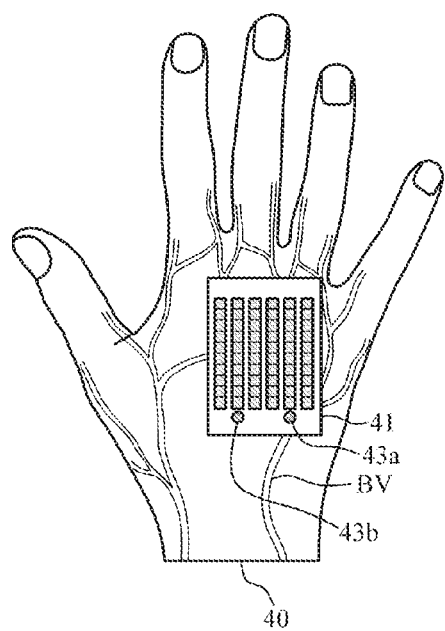

FIG. 3 is a block diagram illustrating a configuration of the processor according to the exemplary embodiment of FIG. 1. FIGS. 4A to 4C are diagrams illustrating configurations of the light source and the detector according to exemplary embodiments. FIGS. 5A to 5F are diagrams illustrating examples of measuring bio-information according to one exemplary embodiments.

Referring to FIGS. 1 and 3, the processor 130 may include a light source driver 310, a signal receiver 320, a signal corrector 330, and a bio-information measurer 340.

When a request for measuring bio-information is received, the light driver 310 drives the first light source 111 and the second light source 112 to emit light to the object OBJ. The light driver 310 may drive the first light source 111 and the second light source 112 sequentially in a time-division manner by referring to a criterion preset for driving the light sources. In this case, the preset criterion may include a pulse duration and light intensity for each light source, the order of driving light sources, etc.

FIG. 4A is a diagram illustrating an optical module 41 including a detector formed as a plurality of photodiode arrays and two light sources disposed on two photodiode lines according to an exemplary embodiment. FIG. 4B is a diagram illustrating an optical module 42 in which two light sources are spaced apart from each other at a specific distance and a plurality of photodiodes 42 are disposed concentrically around the two light sources according to an exemplary embodiment. In FIGS. 4A and 4B the light sources may be, for example, LEDs. FIGS. 4A and 4B illustrate exemplary embodiments of the optical module, but aspects of the exemplary embodiments are not limited thereto. FIG. 4C is a diagram illustrating a case in which the optical module 41 according to the exemplary embodiments of FIGS. 4A and 4B is in contact with the back of the hand.

Referring to FIGS. 4A to 4C, the light source driver 310 may determine a first light source 43a for emitting light to a first region BV of the back of the hand 40 through which a blood vessel passes and a second light source 43b for emitting light to a second region through which a blood vessel does not pass. If there are three or more light sources, the light source driver 310 may divide the light sources into a first light source group for emitting light to the first region and a second light source group for emitting light to the second region and determine one or more light sources to be driven from each of the groups.

For example, the light source driver 310 may determine the light sources for emitting light to the first region and the second region by referring to preset criteria. In this case, the preset criteria may include optimal positions, for example, the back of the hand, a wrist, etc., of an object for the optical module to be in contact with and information about the light sources or light source groups for emitting light to the first region and the second region.

According to an exemplary embodiment, the light source driver 310 may analyze a distribution of a blood vessel region and a non-blood vessel region based on the real-time image of the object 40 and determine the first light source 43a for emitting light to the first region, which is a blood vessel region BV, and the second light source 43b for emitting light to the second region, which is a non-blood vessel region.

Referring to FIGS. 1 and 3, the signal receiver 320 may be electrically connected to the detector 120. When the detector 120 detects the first scattered light signal scattered from the object irradiated by the first light source 111 and the second scattered light signal scattered from the object irradiated by the second light source 112 and outputs the first electrical signal and the second electrical signal which are converted from the first scattered light signal and the second scattered light signal, respectively, the signal receivers 320 may sequentially receive the first electrical signal and the second electrical signal. In this case, the signal receiver 320 may perform preprocessing of the first electrical signal or the second electrical signal, such as normalizing, smoothing treatment, etc., when necessary.

For example, when the light source driver 310 drives the first light source 111 and receives the electrical signal from the detector 120, the signal receiver 320 may determine that the electrical signal is a first electrical signal that corresponds to the first scattered light signal detected from the blood vessel region. In addition, when the light source driver 310 drives the second light source 112 after an elapse of a predetermined period of time and receives an electrical signal from the detector 120, the signal receiver 320 may determine that the electrical signal is a second electrical signal that corresponds to the second scattered light signal detected from the non-blood vessel region.

When a plurality of first electrical signals and second electrical signals are received from the plurality of photodiodes, the signal receiver 320 may select some of the first electrical signals and some of the second electrical signals to be used in measuring bio-information from among the plurality of first electrical signals and second electrical signals.

Figure 5B:
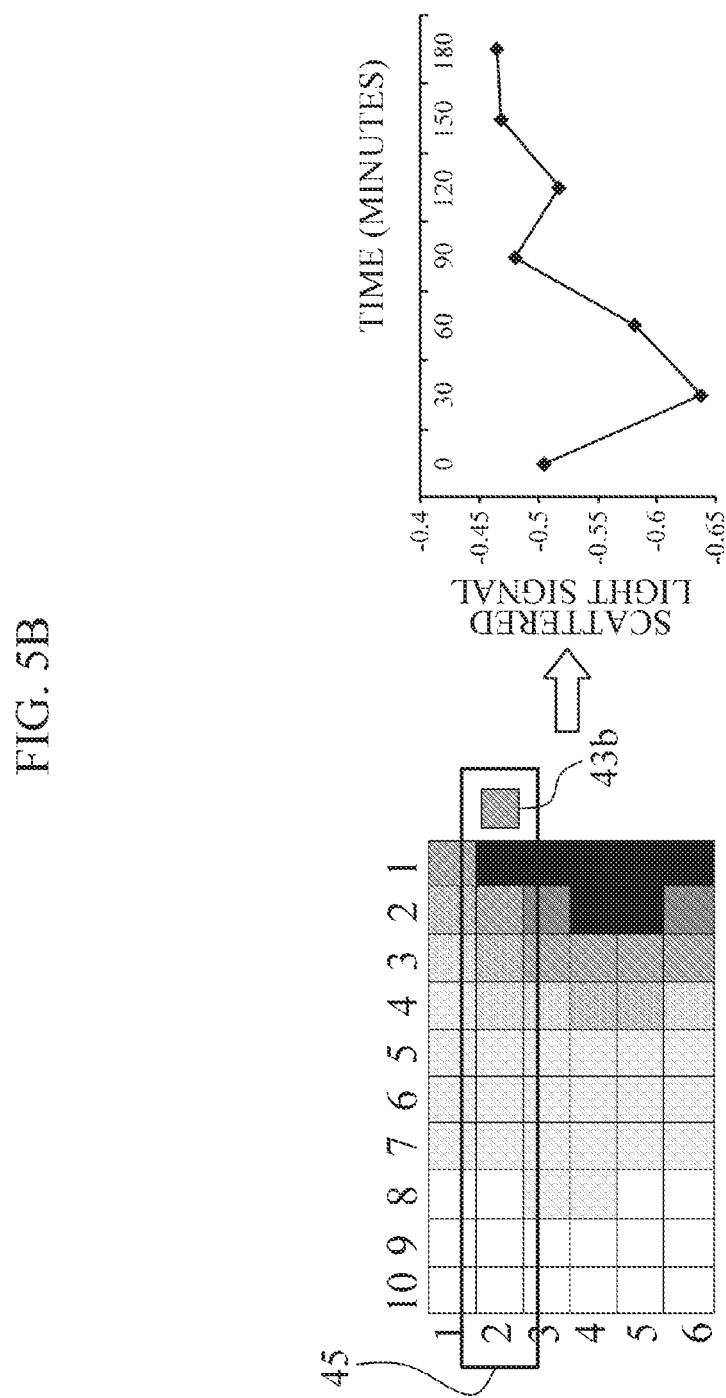
Figure 10:
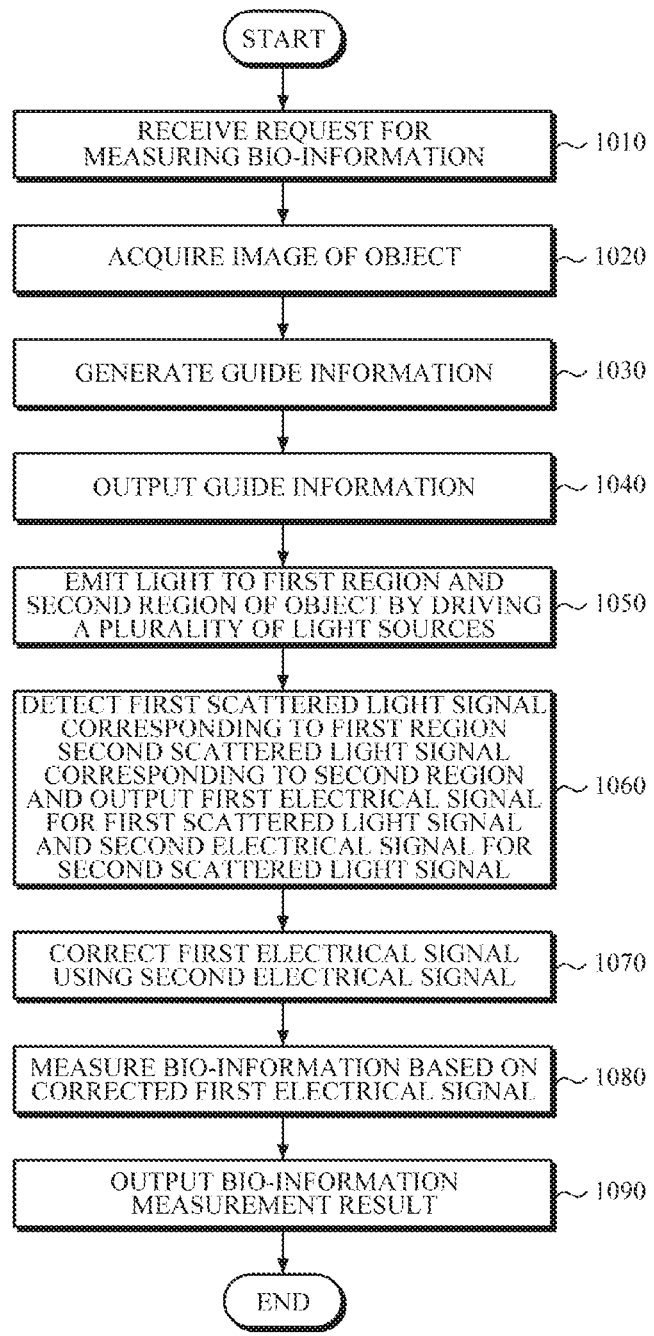
FIG. 10 is a flowchart illustrating a method of measuring bio-information according to an exemplary embodiment.

For example, referring to FIG. 5A, 10 scattered light signals detected by 10 photodiodes belonging to a photodiode line 44 of a photodiode array on which a first light source 43a is disposed may be selected as first scattered light signals to be used in measuring bio-information. In addition, referring to FIG. 5B, 10 scattered light signals detected by 10 photodiodes belonging to a photodiode line 45 of the photodiode array on which a second light source 43b is disposed may be selected as second scattered light signals to be used in measuring bio-information.

However, aspects of the present disclosure are not limited to the photodiodes on which the first light source 43a and the second light source 43b are disposed or the use of only some of the scattered light signals for calculating a scattering coefficient. For example, the scattered light signals detected by all of the photodiode array may be utilized, or scattered light signals of some of the photodiodes belonging to the entire photodiode array may be selected according to various criteria as described below.

For example, a predetermined number of scattered light signals may be selected based on the intensities of the first scattered light signals and the second scattered light signals. The predetermined number may be, but not limited to, 2, and may be set differently according to a computing performance of the device 100. Alternatively, similarity among a plurality of first scattered light signals or similarity among the plurality of second scattered light signals may be calculated, and the first scattered light signals or the second scattered light signals whose similarity satisfies a predetermined criterion may be selected. In this case, the similarity may include at least one of a Euclidean distance, a Pearson correlation coefficient, a Spearman correlation coefficient, and cosine similarity.

The signal corrector 330 may correct the first electrical signal based on the second electrical signal. As described above, the first electrical signal based on the first scattered light signal detected from the blood vessel region includes a change due to noise, and thus, by correcting the first electrical signal based on the second electrical signal based on the second scattered light signal detected from the non-blood vessel region in which a change due to noise in only reflected, noise from the first electrical signal may be removed.

For example, the signal corrector 330 may correct the first electrical signal by taking into consideration a rate of change of the second electrical signal at the same point in time based on a time axis.

First, the signal corrector 330 may calculate a first scattering coefficient and a second scattering coefficient based on a plurality of first electrical signals and a plurality of second electrical signals, respectively. In this case, the scattering coefficient may represent a numerical value by which intensity of light is reduced by scattering while the light emitted from the light source travels along a unit length. For example, the scattering coefficient may be defined as a ratio of the intensities of scattered lights detected by a plurality of photodiodes or a value proportional to the ratio. In addition, the scattering coefficient may be calculated by also taking into consideration a distance from each of the photodiodes to the light source. Alternatively, a representative value of the intensities of a plurality of electrical signals may be calculated as the scattering coefficient. In this case, the representative value of the intensities of the plurality of electrical signals may be calculated based on various criteria, such as the greatest signal intensity, an average of the signal intensities, a median value of the signal intensities, etc. For example, when the signal corrector 330 calculates the scattering coefficients using the scattered light signal detected by one photodiode, the signal corrector 330 may calculate the first scattering coefficient and the second scattering coefficient through Equations 1 and 2 as below.

$$\ln\left\{\rho^2 \frac{R(\rho)}{S_0}\right\} = -\mu_{\text{eff}}\rho + \ln\frac{3\mu_a}{2\pi\mu_{\text{eff}}} \quad (1)$$

$$\ln\left\{\rho^3 \frac{R(\rho)}{S_0}\right\} = -\mu_{\text{eff}}\rho + \ln\frac{1}{2\pi\mu_s} \quad (2)$$

Here, $R(\rho)$ denotes an intensity of light detected by a photodetector, and $\rho$ denotes a distance between a light source and the photodetector. $\mu_a$ denotes an absorption coefficient, $\mu_{\text{eff}}$ denotes an effective attenuation coefficient, and $S_0$ denotes an intensity of light emitted by a light source. $\mu_s$ denotes the scattering coefficient.

According to an exemplary embodiment, when the signal corrector 330 calculates the scattering coefficient using scattered light signals detected by two photodiodes disposed at different distances from a light source which emits light, the signal corrector 330 may calculate the scattering coefficient through Equation 3 as below.

$$\mu_s = \frac{1}{3\mu_a}\left\{\frac{1}{\rho_2 - \rho_1}\ln\frac{\rho_1^2 R(\rho_1)}{\rho_2^2 R(\rho_2)}\right\}^2 \quad (3)$$

Here, $\rho_1$ denotes a distance between the light source and a first photodetector and $\rho_2$ denotes a distance between the light source and a second photodetector. $R(\rho_1)$ denotes an intensity of light detected by the first photodetector and $R(\rho_2)$ denotes an intensity of light detected by the second photodetector. $\mu_s$ denotes the scattering coefficient. As described above, the scattering coefficient calculation equation may be different depending on the number of photodiodes used to detect light emitted from the light source.

FIG. 5A is a diagram illustrating an example of a plurality of first scattered light signals detected by a photodiode array by emitting light to the first region at intervals of 30 minutes using the first light source 43a. A graph shows a first scattering coefficient calculated using a plurality of first scattered light signals detected by a photodiode line 44 on which the first light source 43a among a plurality of first scattered light signals detected at each point in time. FIG. 5B is a diagram illustrating an example of a plurality of second scattered light signals detected by a photodiode array by emitting light to the second region at intervals of 30 minutes using the second light source 43b. A graph shows a second scattering coefficient calculated using a plurality of second scattered light signals detected by a photodiode line 45 on which the second light source 43b is disposed among second scattered light signals detected at each point in time.

Then, when the first scattering coefficient and the second scattering coefficient are calculated, the signal corrector 330 may correct the first scattering coefficient based on the calculated second scattering coefficient. For example, the signal corrector 330 may calculate each of a rate of change of the first scattering coefficient and a rate of change of the second scattering coefficient during a time period from a first time point to a second time point based on a time axis. In addition, the signal corrector 330 may correct the first scattering coefficient at the second time point by taking into consideration the calculated rate of change of the first scattering coefficient and the calculated rate of change of the second scattering coefficient.

Meanwhile, when the first time point and the second time point are not close to each other, for example, when the first time point is a 0-minute point and the second time point is a 60-minute point, the signal corrector 330 may calculate a statistical value, such as an average, a median value, etc., of a rate of change of the scattering coefficient during the first period from the first time point to the next time point, 30-minute point, and a rate of change of the scattering coefficient during the second period from the 30-minute point to the second time point, i.e., a 60-minute point, and correct the first scattering coefficient at the second time point (60 minutes) based on the calculated statistical value.

Figure 5C:
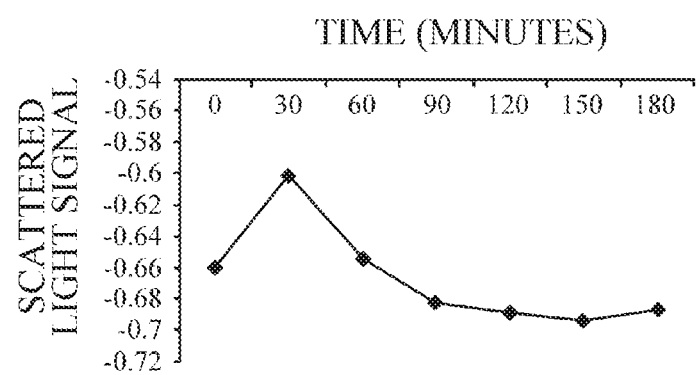

FIG. 5C is a diagram illustrating a result of correcting the first scattering coefficient by the signal corrector 330 based on the first scattering coefficients and the second scattering coefficients at each point in time shown in FIGS. 5A and 5B. For example, referring to FIG. 5A, the first scattering coefficient is reduced by approximately 16% during a period from the first time point (0 minute) to the second time point (30 minutes). Referring to FIG. 5B, the second scattering coefficient is reduced by approximately 26% during a period from the first time point (0 minute) to the second time point (30 minutes). Here, when the change of the second scattering coefficient is considered as being caused by noise, it may be regarded that the decrement (26%) of the second scattering coefficient is included in the decrement (16%) of the first scattering coefficient. Thus, referring to FIG. 5C, the corrected scattering coefficient at the second time point (30 minutes) may be calculated by considering the increment of 10% (26%–16%) of the first scattering coefficient. In this case, the signal corrector 330 may apply different weights to the rate of change of the first scattering coefficient and the rate of change of the second scattering coefficient, and correct the first scattering coefficient using each of the weighted rates of change.

When the first scattering coefficient at a current measurement time is corrected by the signal corrector 330, the bio-information measurer 340 may measure bio-information based on the corrected first scattering coefficient. For example, the bio-information may be estimated by inputting the corrected first scattering coefficient to a bio-information measurement model. In this case, the bio-information measurement model may be generated in the form of a linear function or a matching table which represents a correlation between the scattering coefficient and a bio-information value. Equation 4 shown below is an example of a linear function that represents a correlation between the triglyceride in blood y and the corrected first scattering coefficient x.

$$y=0.0002x-0.0403 \quad (4)$$

Figure 5D:
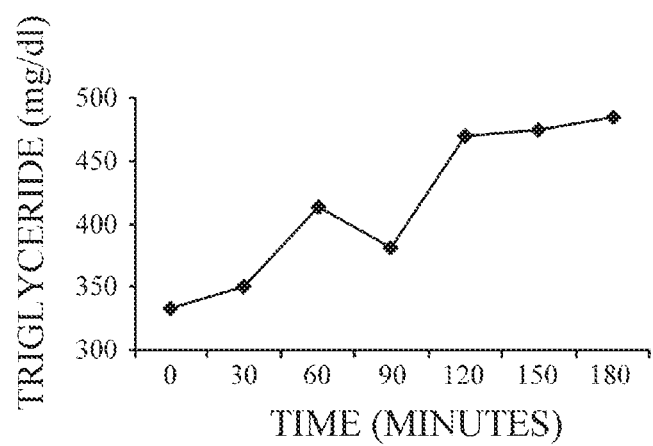
Figure 5E:
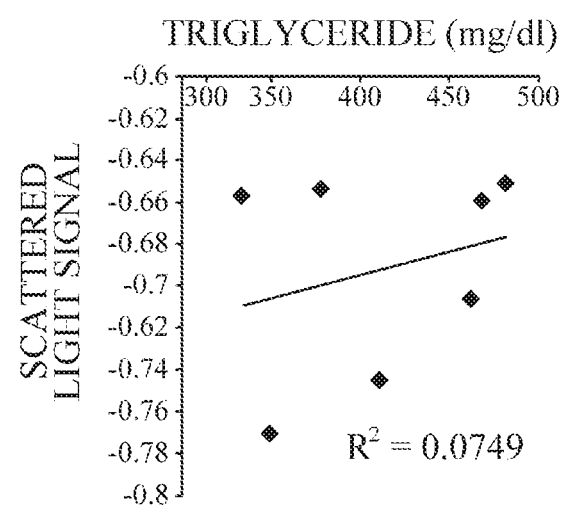
Figure 5F:
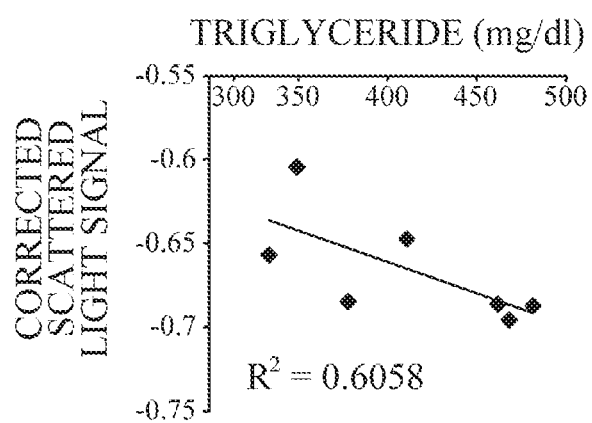

FIG. 5D is a diagram illustrating an actual concentration of triglyceride in blood measured at predetermined time intervals. Referring to FIG. 5E, the first scattered light signal of FIG. 5A before correction and the actual triglyceride exhibit a correlation of $R^2=0.0749$, and referring to FIG. 5F, the corrected first scattered light signal of FIG. 5C and the actual triglyceride exhibit a correlation of $R^2=0.6058$. Thus, it can be seen that the correlation between the corrected first scattered light signal and the actual triglyceride is significantly higher than that in the case of using the first scattered light signal before correction.

Figure 6:
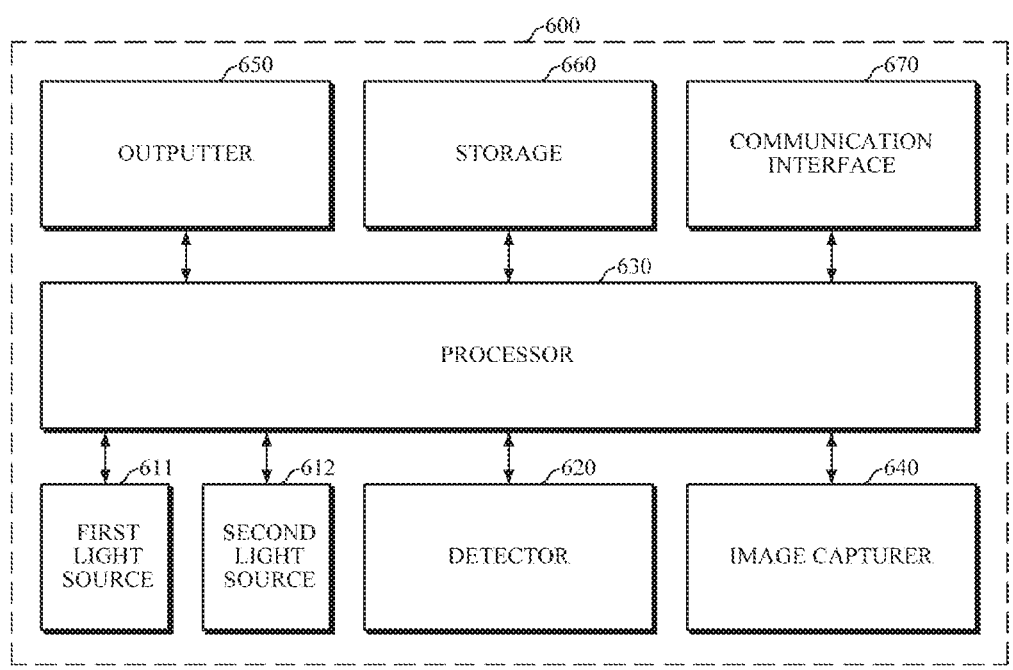
FIG. 6 is a block diagram illustrating an apparatus for measuring bio-information according to an exemplary embodiment.
Figure 7:
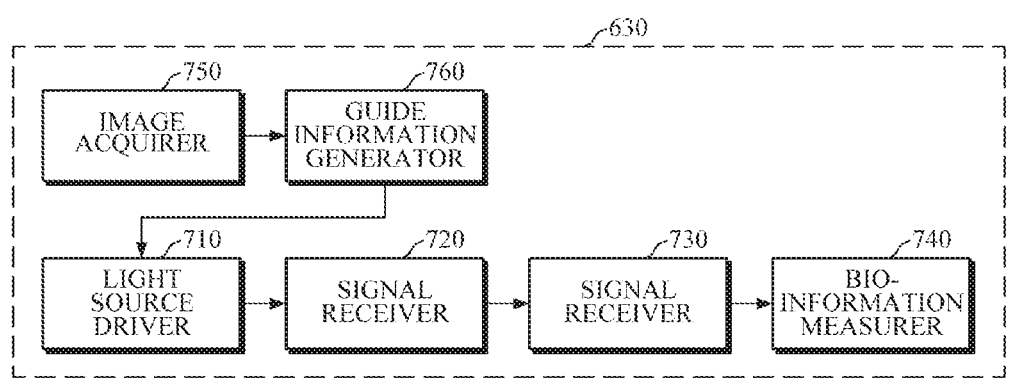
FIG. 7 is a block diagram illustrating a configuration of a processor according to the exemplary embodiment of FIG. 6.
Figure 8:
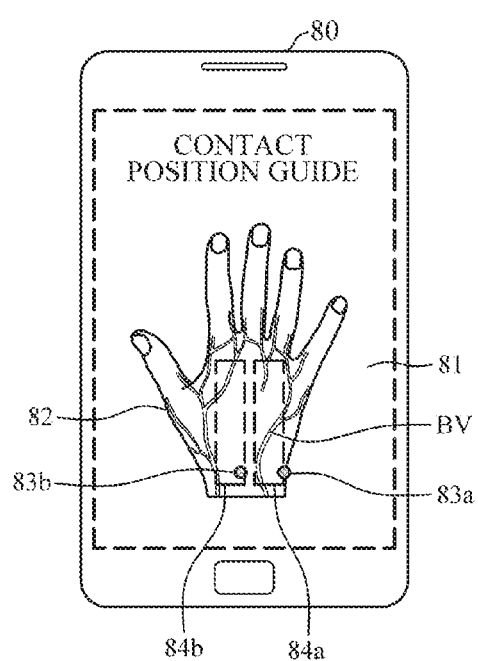
FIG. 8 is a diagram for describing an example of guiding a contact position in the apparatus for measuring bio-information according to an exemplary embodiment.

FIG. 6 is a block diagram illustrating an apparatus for measuring bio-information according to an exemplary embodiment. FIG. 7 is a block diagram illustrating a configuration of a processor according to the exemplary embodiment of FIG. 6. FIG. 8 is a diagram for describing an example of guiding a contact position in the apparatus for measuring bio-information according to an exemplary embodiment.

Referring to FIG. 6, the apparatus 600 for measuring bio-information includes a first light source 611, a second light source 612, a detector 620, a processor 630, an image capturer 640, an outputter 650, a storage 660, and a communication interface 670. Corresponding configurations of the first light source 611, the second light source 612, the detector 620, and the processor 630 have been described in detail with reference to FIGS. 1 to 5F, and thus hereinafter, description will be given of configurations that are not redundant.

When a request for measuring bio-information is received from a user, the processor 630 may generate guide information about a position of an object to be contacted by an optical module of the apparatus 600.

Referring to FIG. 7, the processor 630 may include a light source driver 710, a signal receiver 720, a signal corrector 730, a bio-information measurer 740, an image acquirer 750, and a guide information generator 760. Configurations of the light source driver 710, the signal receiver 720, the signal corrector 730, and the bio-information measurer 740 have been described in detail above.

The image acquirer 750 may acquire a real image of an object by controlling the image capturer 640 according to the request for measuring bio-information, or acquire an image of the object by referring to the storage 660.

The guide information generator 760 may generate guide information based on the image of the object acquired by the image acquirer 750. For example, a guide image may be generated by superimposing visual information that represents the first region or the second region on the acquired image of the object. In addition, the guide image may be generated by superimposing visual information that represents the first light source 611 or the second light source 612 on the acquired image of the object. In this case, when the real image of the object is acquired from the image capturer 640, the guide information generator 760 may extract blood vessel distribution information by analyzing the real image of the object and generate an augmented reality (AR) image by superimposing the visual information representing the first region or the second region and the visual information representing the first light source 611 or the second light source 612 based on the extracted blood vessel distribution information.

The image capturer 640 may acquire an image of the object for generating the guide information about the contact position of the object under the control of the processor 630. The image capturer 640 may not be mounted in the apparatus 600 for measuring bio-information if necessary.

The outputter 650 may output and provide a processing result of the processor 630 to the user. For example, the measured bio-information, for example, the triglyceride level, may be output visually to a display or be output as an audio signal. In addition, when the triglyceride level is outside of a predetermined range, warning information may be output. In this case, the warning information may be provided to the user by changing color of the triglyceride level output to the display or by tactile sensation or vibration through a haptic module.

In addition, the outputter 650 may output the guide information generated by the processor 630. For example, FIG. 8 is a diagram illustrating the apparatus 600 for measuring bio-information in the form of a mobile terminal 80, in which the guide image may be output to a display 810 of the mobile terminal 80. In this case, as shown in FIG. 8, a guide image may be displayed in such a manner that visual information 84a representing the first region, visual information 84b representing the second region, and visual information representing the first light source 83a or the second light source 83b are superimposed on an image 82 of the object. FIG. 8 illustrates an example in which the first light source is not accurately placed in the first region. The user may adjust the position of the first light source to be accurately located in the first region by moving the mobile terminal 80 while viewing the guide information.

A variety of reference information or the processing result of the processor 630 may be stored in the storage 660. For example, the reference information may include driving conditions for the plurality of light sources, a bio-information measurement model, information on appropriate position of an object, object-position-specific images, and user information, such as age, sex, and health status of the user.

In this case, the storage 660 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk.

The communication interface 670 may establish a communication connection with an external device, transmit the detected first electrical signal and second electrical signal, the correction result, and the processing result of the processor 630 to the external device, and receive information, such as a bio-information measurement model, from the external device. In this case, the communication interface 670 may utilize Bluetooth communication, Bluetooth low energy (BLE) communication, near-field communication unit (NFC), wireless local access network (Wi-Fi) communication, ZigBee communication, infrared data association (IrDA) communication, Wi-Fi direct (WFD) communication, ultra-wideband (UWB) communication, Ant+ communication, Wi-Fi communication, $3^{rd}$ generation (3G) communication, $4^{th}$ generation (4G) communication, and $5^{th}$ generation (5G) communication technologies. However, the type of communication technologies are not limited to the above examples.

Figure 9:
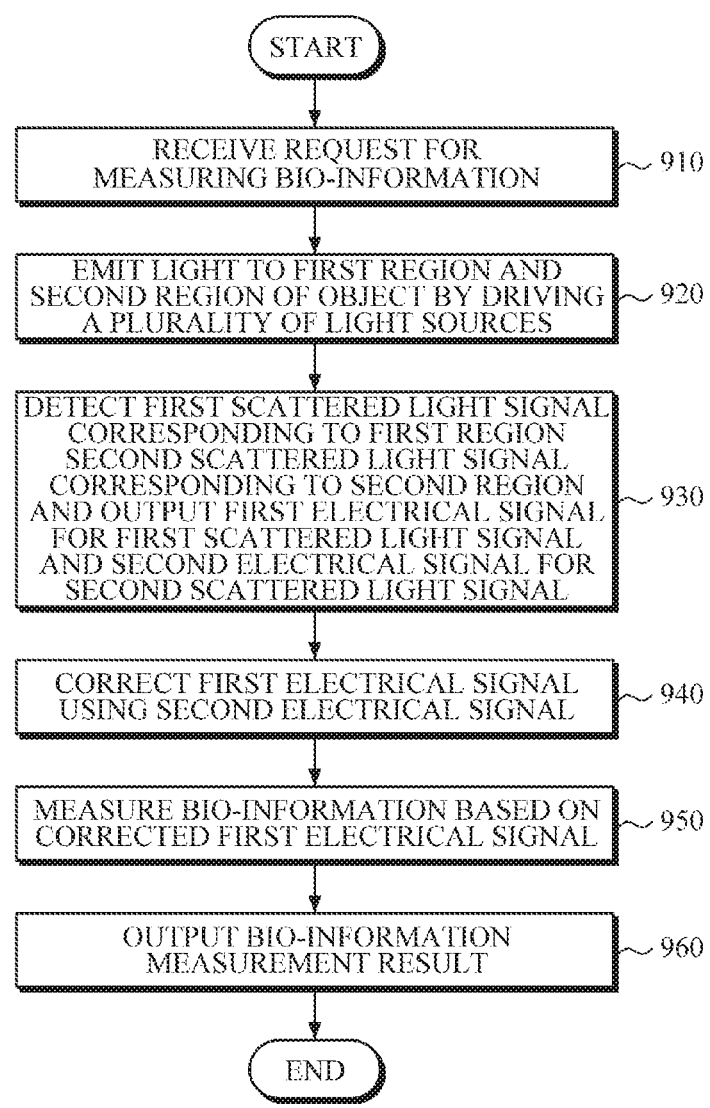
FIG. 9 is a flowchart illustrating a method of measuring bio-information according to an exemplary embodiment.

FIG. 9 is a flowchart illustrating a method of measuring bio-information according to an exemplary embodiment.

The method of FIG. 9 may be an example embodiment of a bio-information measurement method performed by the apparatus 100 for measuring bio-information according to the exemplary embodiment of FIG. 1.

When a request for measuring bio-information is received in 910, the apparatus 100 for measuring bio-information may drive a plurality of light sources to emit light to a first region and a second region of an object in 920. In this case, the first region of the object may be a blood vessel region through which a blood vessel passes, and the second region may be a non-blood vessel region through which a blood vessel does not pass. The plurality of light sources may be sequentially driven in a time-division manner. For example, a light source for emitting light to the first region may be first driven and a light source for emitting light to the second region may be driven after an elapse of a predetermined period of time.

Then, the apparatus 100 may detect a first scattered light signal corresponding to the first region and a second scattered light signal corresponding to the second region in 930. In this case, a detecting sensor may include a plurality of photodiodes and the plurality of photodiodes may be disposed at different distances from the plurality of light sources. In this case, the apparatus 100 may convert the detected first scattered light signal and second scattered light signal into a first electrical signal and a second electrical signal, respectively, and output the first and second electrical signals. Thereafter, the first electrical signal may be corrected using the second electrical signal in 940. For example, the apparatus 100 may calculate a first scattering coefficient and a second scattering coefficient based on the first electrical signal and the second electrical signal. Then, in order to correct the first scattering coefficient at a current time, a rate of change of the first scattering coefficient and a rate of change of the second scattering coefficient during a period from a previous time point to the current time point are calculated, and the first scattering coefficient may be corrected by taking into consideration each of the calculated rates of change of the scattering coefficients.

In this case, the apparatus 100 may select at least some of the first scattered light signals detected by the plurality of photodiodes or at least some of the detected second scattered light signals, and correct the first electrical signal based on the second electrical signals corresponding to the selected second scattered light signals.

Then, bio-information may be measured based on the corrected first electrical signal in 950. For example, the bio-information may be measured by inputting the corrected first scattering coefficient into the bio-information measurement model.

Then, a bio-information measurement result may be output and provided to the user in 960.

FIG. 10 is a flowchart illustrating a method of measuring bio-information according to an exemplary embodiment.

The method shown in FIG. 10 is an exemplary embodiment of a bio-information measurement method performed by the apparatus 600 for measuring bio-information according to the exemplary embodiment of FIG. 6.

When a request for measuring bio-information is received in 1010, the apparatus 600 for measuring bio-information may acquire an image of an object in 1020. For example, the apparatus 600 may control an image sensor to acquire a real image of the object, or may acquire an image of the object stored in a storage module.

Then, the apparatus 600 generates guide information based on the acquired image of the object in 1030 and outputs the generated guide information in 1040. In this case, the guide information may include a blood vessel region of the object and a guide image to guide a light source to be accurately in contact with the blood vessel region. The apparatus 600 may generate the guide image by superimposing visual information representing a first region or a second region or visual information representing a first light source 611 or a second light source 612 on the image of the object. In this case, the guide image may be a still image or an AR image generated based on the real image of the object.

Then, when light sources are positioned accurately in the first region and the second region of the object, the apparatus 600 may control the plurality of light sources to emit light to the first region and the second region in 1050. At this time, the plurality of light sources may be sequentially driven in a time-division manner, starting from the first light source 611 which emits light to the first region.

Then, the apparatus 600 may detect a first scattered light signal corresponding to the first region and a second scattered light signal corresponding to the second region in 1060. In this case, a detecting sensor may include a plurality of photodiodes and the plurality of photodiodes may be disposed at different distances from the plurality of light sources. When the first scattered light signal and the second scattered light signal are detected, the apparatus 100 may convert the detected first and second scattered light signals into a first electrical signal and a second electrical signal, respectively.

Then, the first electrical signal may be corrected using the second electrical signal in 1070. For example, the apparatus 600 may calculate a first scattering coefficient and a second scattering coefficient based on the first electrical signal and the second electrical signal, and correct the first scattering coefficient by taking into consideration a rate of change of the first scattering coefficient and a rate of change of the second scattering coefficient during a period from a previous time point to a current time point.

Then, bio-information may be measured based on the corrected first electrical signal in 1080. For example, the bio-information may be measured by inputting the corrected first scattering coefficient into a bio-information measurement model.

Then, a bio-information measurement result may be output and provided to the user in 1090.

Figure 11:
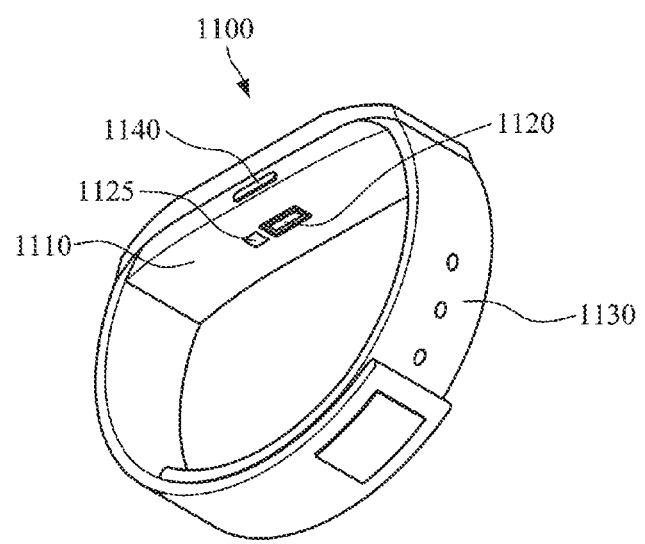
FIG. 11 is a diagram illustrating a wearable device according to an exemplary embodiment.
Figure 12:
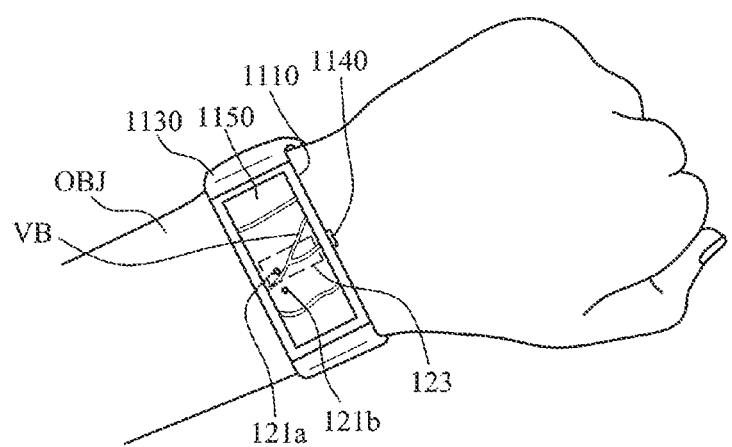
FIG. 12 is a diagram for describing an example of guiding a contact position in the wearable device according to an exemplary embodiment.

FIG. 11 is a diagram illustrating a wearable device according to an exemplary embodiment. FIG. 12 is a diagram for describing an exemplary embodiment of guiding a contact position in the wearable device. FIGS. 11 and 12 illustrate a smartwatch or a smart band type wearable device in which the above-described apparatus 100 or 600 for measuring bio-information is mounted, but the type of the wearable device is not limited thereto.

Referring to FIG. 11, the wearable device 1100 includes a main body 1110 in which the above-described configurations of the apparatus 100 or 600 for measuring bio-information may be mounted, and a strap 1130 flexibly formed to be wrapped around a user's wrist. In this case, a battery for supply power to the wearable device 1100 may be embedded in the main body 1110 or the strap 1130.

An optical unit 1120 may be mounted on a rear surface of the main body 1110 in contact with the user's wrist so as to be exposed to the outside. The optical unit 1120 may include a plurality of light sources and a detecting sensor. Some of the plurality of light sources may emit light to a first region of an object and the other light sources may emit light to a second region of the object. In this case, the first region may be a blood vessel region and the second region may be a non-blood vessel region. Each of the plurality of light sources may emit light of a different wavelength or light of a same wavelength. The detecting sensor may include a plurality of photodiodes.

In addition, an image capturer 1125 may be mounted on the rear surface of the main body 1110. The image capturer 1125 may acquire an image of an upper part of the wrist for generating guide information according to the control of a processor.

The processor mounted in the main body 1110 may be electrically connected to the optical unit 1120 and measure bio-information on the basis of a first scattered light signal and a second scattered light signal which are detected by the optical unit 1120. In this case, more accurate bio-information may be measured by removing noise from the first scattered light signal on the basis of the second scattered light signal measured from the non-blood vessel region. In this case, the optical unit 1120 may convert the detected first scattered light signal and second scattered light signal into a first electrical signal and a second electrical signal, respectively, and output the first and second electrical signals to the processor.

In addition, the processor may receive a bio-information measurement command input through a touch interface of an operator 1140 or a display 1150. When the bio-information measurement command is input, the processor may control the image capturer 1125 to acquire a real image of the upper part of the wrist (OBJ) as shown in FIG. 12.

When the real image is acquired, the processor may analyze a blood vessel region BV and generate a guide image on which visual information 123 representing a first region is superimposed. In addition, the processor may generate the guide image by taking into consideration a position of the optical unit 1120 mounted on the rear surface of the main body 1110 and superimposing visual information 121a representing a light source for emitting light to the first region or visual information 121b representing a light source for emitting light to a second region on the real image.

The operator 1140 may be mounted on a side surface of the main body 1110. The user may operate the operator 140 to input various commands and the operator 1140 may transmit the command input by the user to the processor. The operator 1140 may be configured to turn on/off a power of the wearable device 1100.

The display 1150 mounted on a front surface of the main body 1110 may output a variety of information including a bio-information measurement result and the guide information, and provide various user experiences offered by the wearable device 1100. The display 1150 may be configured as a touch panel. The display 1150 may receive a user command input through the user interface and transmit the user command to the processor.

The current embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

While one or more embodiments have been described with reference to the figures, it will be understood by those of ordinary skill in the art that various changes in form and details may be made therein without departing from the spirit of the disclosure, the scope of which is defined in the following claims and their equivalents.

What is claimed is:

1. An apparatus to measure bio-information, the apparatus comprising:
    a plurality of light sources configured to emit light to a first region and a second region of an object;
    a detector configured to detect a first scattered light signal reflected from the first region and a second scattered light signal reflected from the second region, and output a first electrical signal corresponding to the first scattered light signal and a second electrical signal corresponding to the second scattered light signal; and
    a processor configured to:
        receive the first electrical signal and the second electrical signal;
        obtain a first scattering coefficient based on the received first electrical signal;
        obtain a second scattering coefficient based on the received second electrical signal;
        obtain a rate of change of the first scattering coefficient and a rate of change of the second scattering coefficient during a time period from a first time point to a second time point based on a time axis;
        correct the first scattering coefficient at the second time point based on the obtained rate of change of the first scattering coefficient and the obtained rate of change of the second scattering coefficient; and
        measure the bio-information based on the corrected first scattering coefficient,
    wherein the detector comprises a plurality of photodiode arrays disposed in a concentric circle shapes at different distances, respectively, from the plurality of light sources provided at a center.

2. The apparatus of claim 1, wherein the first region comprises a blood vessel region and the second region comprises a non-blood vessel region.

3. The apparatus of claim 1, wherein the processor is further configured to sequentially drive each of the plurality of light sources in a time-division manner.

4. The apparatus of claim 1, wherein the processor is further configured to select a first light source among the plurality of light sources to emit light to the first region and a second light source from among the plurality of light sources to emit light to the second region from the plurality of light sources based on a preset criteria, and sequentially drive the first light source and the second light source to emit light.

5. The apparatus of claim 1, wherein the plurality of light sources comprise at least one of a light emitting diode (LED) and a laser diode which emit light of an infrared band.

6. The apparatus of claim 1, further comprising a communication interface configured to transmit at least one of the first electrical signal, the second electrical signal, the corrected first scattering coefficient, and the measured bio-information to an external device.

7. The apparatus of claim 1, wherein the processor is further configured to generate guide information corresponding to contact positions on the object of the plurality of light sources based on receiving a request to measure the bio-information.

8. The apparatus of claim 7, wherein the guide information comprises a guide image generated by superimposing visual information representing at least one of the first region and the second region or visual information representing at least one of the plurality of light sources on an image of the object.

9. The apparatus of claim 7, further comprising an outputter configured to output at least one of the first electrical signal, the second electrical signal, the corrected first scattering coefficient, the measured bio-information, and the guide information.

10. The apparatus of claim 1, further comprising a storage configured to store at least one of value of the first electrical signal, value of the second electrical signal, the corrected first scattering coefficient signal, and the measured bio-information.

11. The apparatus of claim 1, wherein the bio-information comprises at least one of blood glucose, cholesterol, triglyceride, skin temperature, protein, and uric acid.

12. A method of measuring bio-information, the method comprising:
    emitting light to a first region and a second region of an object by a plurality of light sources;
    detecting a first scattered light signal reflected from the first region and a second scattered light signal reflected from the second region, and outputting a first electrical signal corresponding to the first scattered light signal and a second electrical signal corresponding to the second scattered light signal;
    receive the first electrical signal and the second electrical signal;
    obtain a first scattering coefficient based on the received first electrical signal;
    obtain a second scattering coefficient based on the received second electrical signal;
    obtain a rate of change of the first scattering coefficient and a rate of change of the second scattering coefficient during a time period from a first time point to a second time point based on a time axis;
    correct the first scattering coefficient at the second time point based on the obtained rate of change of the first scattering coefficient and the obtained rate of change of the second scattering coefficient; and
    measure the bio-information based on the corrected first scattering coefficient.

13. The method of claim 12, wherein the first region comprises a blood vessel region and the second region comprises a non-blood vessel region.

14. The method of claim 12, wherein the emitting of the light comprises sequentially driving the plurality of light sources in a time-division manner.

15. The method of claim 12, further comprising outputting the measured bio-information.

16. The method of claim 12, further comprising:
    generating guide information corresponding to contact positions on the object of the plurality of light sources based on receiving a request to measure the bio-information; and
    outputting the generated guide information.

17. A wearable device comprising:
    a main body;
    a strap connected to the main body and configured to fix the main body to an object;
    an optical apparatus disposed in the main body and configured to emit light to a first region and a second region of the object, detect a first scattered light signal reflected from the first region and a second scattered light signal reflected from the second region, and output a first electrical signal corresponding to the first scattered light signal and a second electrical signal corresponding to the second scattered light signal; and
    a processor disposed in the main body and configured to:
    receive the first electrical signal and the second electrical signal;
    obtain a first scattering coefficient based on the received first electrical signal;
    obtain a second scattering coefficient based on the received second electrical signal;
    obtain a rate of change of the first scattering coefficient and a rate of change of the second scattering coefficient during a time period from a first time point to a second time point based on a time axis;
    correct the first scattering coefficient at the second time point based on the obtained rate of change of the first scattering coefficient and the obtained rate of change of the second scattering coefficient; and
    measure the bio-information based on the corrected first scattering coefficient.

18. The wearable device of claim 17, wherein the first region comprises a blood vessel region and the second region comprises a non-blood vessel region.

19. The wearable device of claim 17, wherein the optical apparatus comprises:
    a plurality of light sources driven in a time-division manner by the processor; and
    a plurality of detectors disposed at different distances from the plurality of light sources, respectively.

20. The wearable device of claim 17, further comprising a display disposed in the main body and configured to display guide information corresponding to a contact position on the object of the optical apparatus based on receiving a request to measure bio-information.

21. The wearable device of claim 20, further comprising an image capturer disposed in the main body and configured to acquire an image of the object to generate the guide information.

22. The wearable device of claim 20, further comprising a communication interface disposed in the main body and configured to receive an image of the object, to generate the guide information, from an external device.

23. An apparatus to measure bio-information, the apparatus comprising:
    a first light source and a second light source configured to emit light to a first region and a second region of an object, respectively;
    a detector configured to detect a first scattered light signal reflected from the first region and a second scattered light signal reflected from the second region, and output a first electrical signal corresponding to the first scattered light signal and a second electrical signal corresponding to the second scattered light signal; and a processor configured to:
  receive the first electrical signal and the second electrical signal;
  obtain a first scattering coefficient based on the received first electrical signal;
  obtain a second scattering coefficient based on the received second electrical signal;
  obtain a rate of change of the first scattering coefficient and a rate of change of the second scattering coefficient during a time period from a first time point to a second time point based on a time axis;
  correct the first scattering coefficient at the second time point based on the obtained rate of change of the first scattering coefficient and the obtained rate of change of the second scattering coefficient; and
  measure the bio-information based on the corrected first scattering coefficient,
wherein the first region comprises a blood vessel region and the second region comprises a non-blood vessel region.

24. The apparatus of claim 23, wherein the first light source comprises at least one light source and the second light source comprises at least one light source.

25. The apparatus of claim 24, wherein the processor is further configured to sequentially drive the first light source and the second light source in a time-division manner.

26. The apparatus of claim 23, wherein the processor is further configured to generate guide information corresponding to contact positions on the object of the first light source and the second light source based on receiving a request to measure the bio-information.

27. The apparatus of claim 26, further comprising an outputter configured to output at least one of the first electrical signal, the second electrical signal, the corrected first scattering coefficient, the measured bio-information, and the guide information,
  wherein the outputter comprises at least one of a display, an audio, a haptic apparatus.

* * * * *